United States Patent [19]
Alfenito

[11] Patent Number: 4,859,302
[45] Date of Patent: Aug. 22, 1989

[54] ELECTROELUTION OF MACROMOLECULES

[75] Inventor: Mark R. Alfenito, Cambridge, Mass.

[73] Assignee: President and Fellows of Harvard College, Cambridge, Mass.

[21] Appl. No.: 112,349

[22] Filed: Oct. 22, 1987

[51] Int. Cl.[4] ............................................. G01N 27/28
[52] U.S. Cl. .................................................. 204/182.8
[58] Field of Search ..................................... 204/182.8

[56] References Cited

U.S. PATENT DOCUMENTS

| | | | |
|---|---|---|---|
| 4,062,731 | 12/1977 | Snoke | 195/62 |
| 4,576,702 | 3/1986 | Peck et al. | 204/299 R |
| 4,576,703 | 3/1986 | Peck | 204/299 R |
| 4,608,147 | 8/1986 | Clad | 204/301 |
| 4,747,918 | 5/1988 | Wassenberg | 204/182.8 |

OTHER PUBLICATIONS

Ahokas, H., *Nucleic Acids Research*, vol. 15, No. 16, p. 6759 (1987).

Primary Examiner—John F. Niebling
Assistant Examiner—Isabelle Rodriquez

[57] ABSTRACT

Macromolecules are electroeluted from a matrix by placing the matrix containing the macromolecules of interest in a container, forcing the matrix toward the tip of the container, e.g., by centrifugation, providing an opening at the tip of the container large enough to pass the component, but not the matrix, inserting that container inside another container, placing an electrode in each container together with enough electrophoresis buffer to immerse each electrode, and applying a voltage across the electrodes for a time and under conditions sufficient to cause the macromolecules but not the matrix to migrate from the first container into the second. A kit for performing the electroelution is also described.

8 Claims, 2 Drawing Sheets

ELECTROELUTION OF MACROMOLECULES

BACKGROUND OF THE INVENTION

This invention relates to electroelution of macromolecules from a matrix.

When biological macromolecules, such as nucleic acids, proteins and the like, are analyzed or purified by electrophoresis, they are recovered from an electrophoretic support matrix, e.g., a gel. Numerous electroelution devices exist to accomplish this objective. For example Peck et al. U.S. Pat. Nos. 4,576,702 and 4,576,703 describe a device consisting of two fluid tight compartments separated by a bridge element. A matrix containing the compound of interest is placed in one compartment, a voltage is applied across electrodes in the two compartments, and the compound of interest travels in the electric field through a system of valves and channels and is recovered in a central cavity in the bridge element. In the device of Clad U.S. Pat. No. 4,608,147, the compound of interest is recovered in a trap formed by two polymer membranes, one of which is permeable to the macromolecule being eluted and one of which is not.

SUMMARY OF THE INVENTION

One aspect of the invention generally features a method for the electroelution of macromolecules from a matrix, involving placing the matrix containing the macromolecules of interest in a container, forcing the matrix toward the tip of the container, e.g., by centrifugation, providing an opening at the tip of the container large enough to pass the component but not the matrix, inserting that container inside another container, placing an electrode in each container together with enough electrophoresis buffer to immerse each electrode, and applying a voltage across the electrodes for a time and under conditions sufficient to cause the macromolecules but not the matrix to migrate from the first container into the second. In that way, the component is separated from the matrix.

In preferred embodiments of the method a filter is provided in the bottom of the first container to prevent gel migration into the second container, and the voltage causes the component to migrate through the filter. The opening is preferably (but not necessarily) provided in the tip after the sample is added. The tip of the first container is tapered, so that the sample is compacted as it is forced toward the tip by centrifugation. The second electrode is annular, and the second container is nested around the first to define a volume between them sufficient to immerse the second electrode, but less than about 250 microliters. The second container is supplied with a lid, and the component is recovered directly from the second container by adding appropriate agents to cause precipitation of the component, closing the container lid, agitating the liquid until precipitation occurs and centrifuging the container contents to collect the precipitated component.

A second aspect generally features a kit for performing the method of the invention. It is composed of a container to receive the matrix containing the macromolecular component of interest, a second container sized and configured to nest loosely around the first container, a first electrode sized to fit inside the second container and outside the first container, and a second electrode sized to fit inside the first container.

In preferred embodiments of the kit the tip of the first container is tapered (becoming narrower at the tip), and is scored to facilitate removal. A filter is provided which is sized to be positioned in the bottom of the first container and which will allow passage of the component but not the matrix into the second container. The second container is supplied with a lid and is configured to fit into a centrifuge. The first electrode is annular and is sized to surround the first container. There is a supply of the first and second containers and filters and a supply of electrode pairs with the electrical circuitry to connect the multiple pairs of electrodes across a single voltage source. The containers and the annular electrode are configured such that a volume of buffer less than about 250 $\mu$l in the second container is sufficient to immerse the electrode.

The invention enables rapid electroelution of macromolecules from a matrix and provides an extremely small volume of electrophoresis buffer in the receiving container. The small recovery volume improves yields, and there is virtually no chance of overrunning the system and losing the sample in a large quantity of electrophoresis buffer. The containers can be disposable which would avoid contamination among successive samples. The method of the invention is appropriate for the recovery of any kind of macromolecule that retains a net charge at physiological pH, e.g., DNA, RNA, or proteins.

Other features and advantages of the invention will be apparent from the following description of the preferred embodiments thereof and from the claims.

DESCRIPTION OF THE PREFERRED EMBODIMENTS

The drawings will first be described briefly.

FIG. 2a is a representation of where a first container tip can be scored and FIG. 2b is a representation of multiple electrode pairs and electrical circuitry to connect those electrode pairs across a single voltage source.

Figure 1:
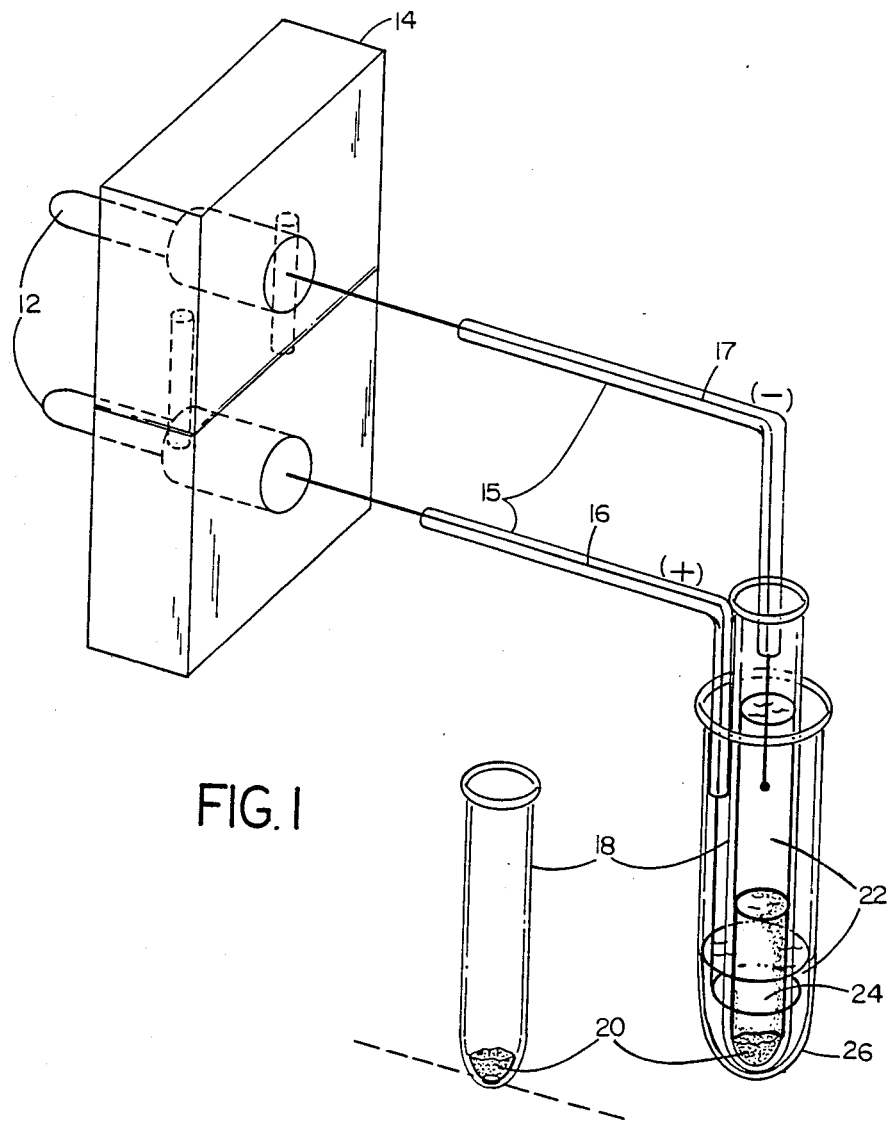
FIG. 1 is a diagrammatic representation of an electroelution device illustrating the principles of the invention.

We now describe the particulars of the preferred embodiments of the invention, referring in detail to FIG. 1. FIG. 1 illustrates a single set of containers and an electrode pair according to the invention, and it is understood that it may be convenient to configure a kit with multiple disposable sets of such containers and multiple sets of electrode pairs.

A small wad of Whatman 3 MM filter paper 20 is placed at the bottom of a small conical (tapered at the tip), plastic, disposable container 18, e.g., the size of a P1000 pipetting tip, that has been sealed off at the end by melting the tip. A section of gel 24, e.g., from an agarose preparative or analytical gel, which contains a DNA sample of interest (the DNA having been visualized under UV light by its fluorescence in the presence of ethidium bromide in the gel) is cut out from the rest of the gel matrix and placed in the container. The container is spun in a microcentrifuge for 5 sec. to compact the gel at the bottom of the tube and avoid the presence of channels through the gel. The base of the container is removed with a razor blade, creating a small opening, e.g., 1 mm.

A second conical, plastic, disposable container 26 is chosen to fit closely, without touching, around the first container. A 1.5 ml eppendorf tube with lid will serve. Two hundred µl of 2X TBE (Maniatis et al., Molecular Cloning, Cold Spring Harbor Laboratory (1982)) as an electrophoresis running buffer 22 is added to the second container. The circular anode (+) 16 is placed into the eppendorf tube so that it is covered by the running buffer. The tip of the first container is then inserted into the collar of the circular anode, in the second container. Six hundred µl of 2X TBE running buffer 22 is put into the first container on top of the gel section. Finally, the cathode (−) 17 is submerged in the running buffer of the first container. To prevent shorting, the electrodes are encased in thin plastic tubing as insulation 15, along those portions that will be outside the buffer solutions.

The electrodes are connected by banana plugs 12 supported in pegged lucite blocks 14 to a power source. The power source is then turned on to 50 V for 20 min. which is usually enough time to electroelute a 10 kilo-base fragment from the gel matrix into the outer container running buffer. After elution is completed, the current is run in the reverse direction for 5 sec. to remove eluted DNA from the electrode. The electrodes are removed, and the inner container is disposed of.

One tenth volume of 3M sodium acetate (about 25 µl) is added to the buffer in the outer container, and the container lid is closed. The buffer and salt are mixed gently with finger vortexing. An equal volume of isopropanol (about 250 µl) is added, and the solution is mixed again. The precipitated DNA is then washed and isolated by standard techniques (Maniatis et al., id.).

A kit to perform the electroelution method contains a first container 18, usually disposable, to receive the sample embedded in the gel matrix, a second container 26, also usually disposable, sized and configured to nest loosely around the first container, an annular electrode 16 sized to fit inside the second container and outside the first container, and a second electrode 17 sized to fit inside the first container. The end of the first container is tapered, the second container is supplied with a lid and is configured to fit into a centrifuge, and the first and second containers and the annular electrode are sized and configured so that the volume of electrophoresis buffer necessary to immerse the annular electrode is less than about 250 µl. The electrodes are supported in pegged lucite blocks 14 and are attached by banana plugs 12 to the appropriate leads to connect them to a voltage source.

In other embodiments of the method the hole in the bottom of the inner container can be present before the gel matrix is added, and packing of the gel at the tip of the container can be accomplished by shaking the container gently as one would a fever thermometer. Sponge or other filtering substances can be substituted for the filter paper in the first container. The time for electroelution is adjusted according to the requirements of the macromolecule being isolated. Less than one hour is generally sufficient. The elution time can be shortened if electrophoresis is performed in a cold room or if the second container is immersed in an ice bath as a high voltage can be used.

Figure 2:
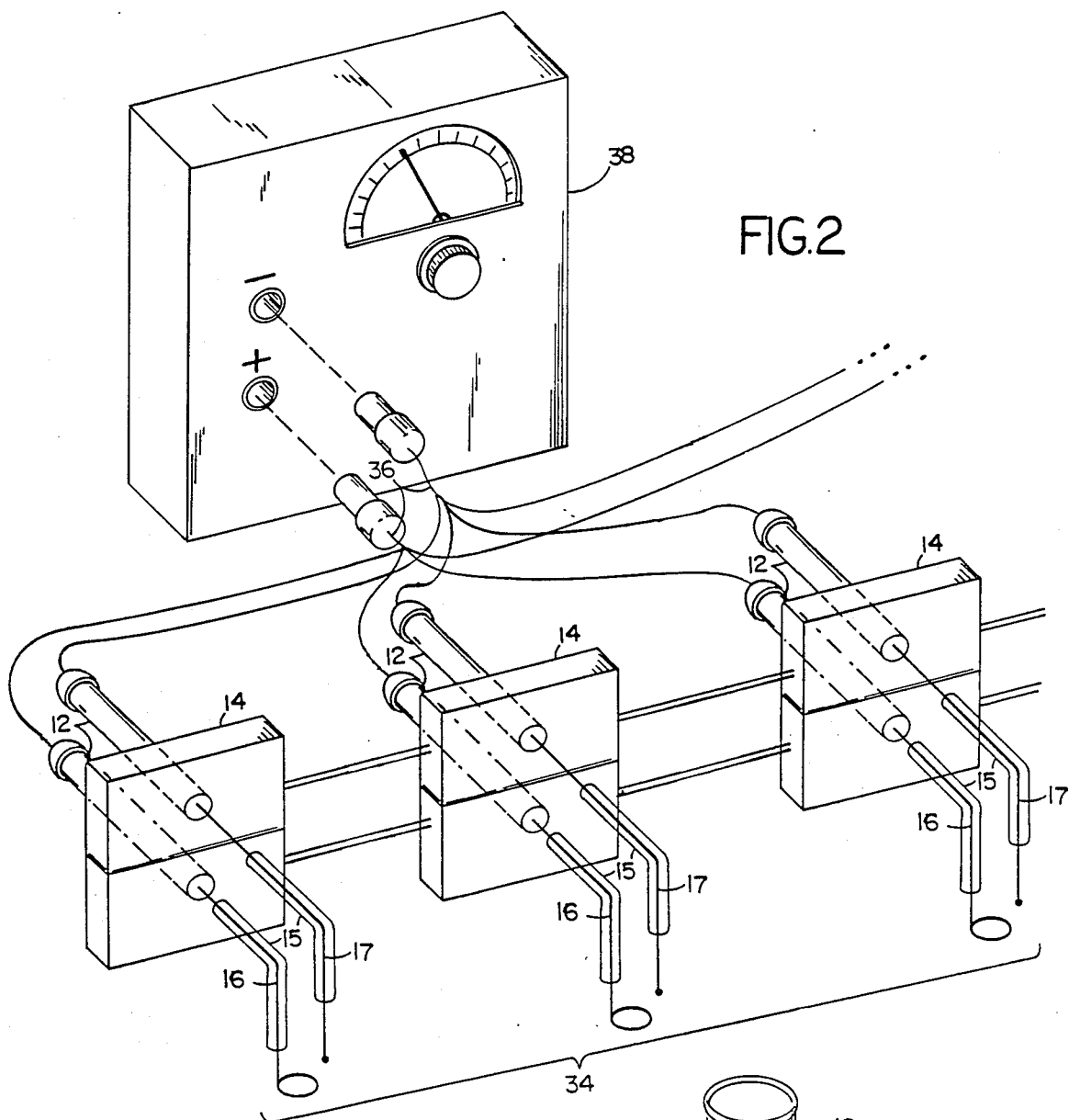
FIG. 2 is a diagrammatic representation of some of the elements of a kit for performing the method of the invention.
Figure 2A:
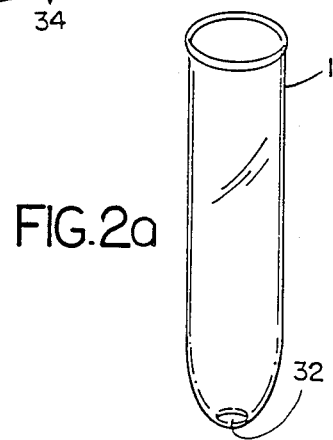

A second embodiment of the kit, illustrated in FIG. 2, contains a first container 18 which is scored at the tip 32 to facilitate removal, and a filter which can be positioned in the bottom of the first container, a supply of disposable first and second containers or multiple electrode pairs 34 and electrical circuitry 36 to connect those electrode pairs across a single voltage source 38. Alternatively, it may be possible to configure the first container with an opening in the tip, large enough to pass the macromolecules but not the matrix.

Other features and embodiments are within the following claims:

I claim:

1. A method for the electroelution of a macromolecular component from a matrix comprising the steps of:
    placing a sample comprising said macromolecular component contained within said matrix in a first container;
    forcing said sample toward the tip of said first container;
    providing an opening at the first container tip large enough to pass said macromolecular component but not said matrix;
    inserting said first container into a second container;
    placing one electrode in said first container and placing a second electrode in said second container, together with enough electrolysis buffer to immerse each said electrode; and
    applying a voltage across said electrodes for a time and under conditions sufficient to cause said macromolecular component to migrate through the opening in said first container tip and into said second container;
    thereby separating said macromolecular component from said matrix.

2. The method of claim 1 comprising
    providing a filter in the bottom of said first container, and
    applying said voltage across said electrodes to cause said macromolecular component to migrate through said filter, said filter preventing migration of said matrix into said second container.

3. The method of claim 1 wherein said opening at said first container tip is provided after inserting said sample and forcing it toward said first container tip.

4. The method of claim 1 wherein the tip of at least said first container is tapered, said method comprising forcing said sample into said tapered tip.

5. The method of claim 1 comprising centrifuging said sample to force it toward the tip of said first container.

6. The method of claim 1 wherein said second electrode is annular and said method comprises positioning said annular electrode around the outside of said first container.

7. The method of claim 1 comprising nesting said second container around said first container, said containers being sized and configured to define a volume between them sufficient to immerse said second electrode, said volume being less than about 250 microliters.

8. The method of claim 1 wherein said second container is supplied with a lid and said method further comprises recovering said macromolecular component directly from said second container by adding to said second container a precipitation agent to cause precipitation of said macromolecular component, closing the lid of said second container, agitating the liquid in said second container until precipitation occurs, and centrifuging the contents of said second container to collect a precipitate of said macromolecular component.

* * * * *